US008658598B2

(12) United States Patent
Accornero et al.

(10) Patent No.: US 8,658,598 B2
(45) Date of Patent: Feb. 25, 2014

(54) RECOMBINANT MELUSIN FUSION PROTEIN AS PHARMACOLOGICAL AGENT IN THE TREATMENT OF HEART PATHOLOGIES

(75) Inventors: Féderica Accornero, Viarigi (IT); Mara Brancaccio, Turin (IT); Guido Tarone, Turin (IT); Giuseppe Lembo, Mugnano del Cardinale (IT); Daniela Carnevale, Cassino (IT)

(73) Assignee: Target Heart Biotec S.R.L., Colleretto Giacosa (TO) (IT)

( * ) Notice: Subject to any disclaimer, the term of this patent is extended or adjusted under 35 U.S.C. 154(b) by 0 days.

(21) Appl. No.: 13/106,251

(22) Filed: May 12, 2011

(65) Prior Publication Data
US 2012/0010386 A1    Jan. 12, 2012

(30) Foreign Application Priority Data
May 12, 2010   (IT) .............................. TO2010A0397

(51) Int. Cl.
*A61P 9/04*    (2006.01)
*A61K 38/16*   (2006.01)
*C07H 21/02*   (2006.01)
*C07K 19/00*   (2006.01)
*C12P 21/02*   (2006.01)

(52) U.S. Cl.
USPC ......... 514/16.4; 435/69.7; 530/350; 530/841; 536/23.4

(58) Field of Classification Search
None
See application file for complete search history.

(56) References Cited

U.S. PATENT DOCUMENTS

2012/0010386 A1*   1/2012   Accornero et al. ........... 530/350

FOREIGN PATENT DOCUMENTS

| EP | 1 575 354 | 9/2005 |
|---|---|---|
| EP | 1 800 696 | 6/2007 |
| WO | WO 2004/056176 A1 | 7/2004 |

OTHER PUBLICATIONS

Futaki et al, 2003. Journal of Molecular Recognition.*
Chugh et al, 2010. 62(3): 183-193.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Italian Search Report for IT Application No. TO2010A000397, dated Oct. 8, 2010.
Written Opinion for IT Application No. TO2010A000397, dated May 12, 2010.
De Acetis, M. et al., "Cardiac Overexpression of Melusin Protects from Dilated Cardiomyopathy Due to Long-Standing Pressure Overload", Circulation Research, vol. 96, No. 10, (May 27, 2005), pp. 1087-1094; and Supplemental Data.
Kwon, J.H. et al., "Protective effect of heat shock protein 27 using protein transduction domain-mediated delivery on ischemia/reperfusion heart inuury", Biochemical and Biophysical Research Commuications, vol. 363, No. 2, (Oct. 1, 2007), pp. 399-404.
Gustafsson, A.B. et al., "TAT Protein transduction Into Isolated Perfused Hearts: TAT-Apoptosis Repressor with Caspase Recruitment Domain is Cardioprotective", Circulation, vol. 106, No. 6, (Aug. 6, 2002), pp. 735-739.
European Search Report issued Sep. 6, 2011 in connection with EP App No. 11165329.1.
De Acetis, M., et al, *Circulation Research*, Vo. 96, No. 10, May 27, 2005, pp. 1087-1094, "Cardiac Overexpression of Melusin Protects From Dilated Cardiomyopathy Due to Long-Standing Pressure Overload," XP-002604243.
Kwon, Jun Hye, et al, *Biochemical and Biophysical Research Communications*, vol. 363, No. 2, (2007) 399-404, "Protective effect of heat shock protein 27 using protein transduction domain-mediated delivery on ischemia/reperfusion heart injury."
Gustafsson, Asa B., et al, *Circulation*, vol. 106, No. 6, Aug. 6, 2002, pp. 735-739, "TAT Protein Transduction Into Isolated Perfused Hearts: TAT-Apoptosis Repressor With Caspase Recruitment Domain Is Cardioprotective," XP-002604244.

* cited by examiner

*Primary Examiner* — Zachary Howard
(74) *Attorney, Agent, or Firm* — Nixon & Vanderhye P.C.

(57) ABSTRACT

A recombinant melusin fusion protein having an improved stability and a capability to reach intracellular compartments as compared to recombinant melusin in vivo, wherein said protein comprises i) a human melusin protein having the amino acid sequence as defined in SEQ ID No.:1, or a homologue thereof having at least 60%, preferably at least 80%, more preferably at least 90% sequence identity to SEQ ID No.:1 and having the function of native melusin protein or a human melusin portion derived from SEQ ID No.:1 or homologue thereof having at least 60%, preferably at least 80%, more preferably at least 90% sequence identity of the melusin portion derived from SEQ ID No.:1 and having the function of native melusin protein and ii) a cell penetrating polypeptide.

6 Claims, 15 Drawing Sheets

Figure 1A

MBP-TAT-MELUSIN

```
         M   K   I   E   E   G   K   L   V   I   W   I   N   G   D   K   G   Y   N   G
   1     atgaaaatcgaagaaggtaaactggtaatctggattaacggcgataaaggctataacggt    60
         L   A   E   V   G   K   K   F   E   K   D   T   G   I   K   V   T   V   E   H
  61     ctcgctgaagtcggtaagaaattcgagaaagataccggaattaaagtcaccgttgagcat   120
         P   D   K   L   E   E   K   F   P   Q   V   A   A   T   G   D   G   P   D   I
 121     ccggataaactggaagagaaattcccacaggttgcggcaactggcgatggccctgacatt   180
         I   F   W   A   H   D   R   F   G   G   Y   A   Q   S   G   L   L   A   E   I
 181     atcttctgggcacacgaccgctttggtggctacgctcaatctggcctgttggctgaaatc   240
         T   P   D   K   A   F   Q   D   K   L   Y   P   F   T   W   D   A   V   R   Y
 241     accccggacaaagcgttccaggacaagctgtatccgtttacctgggatgccgtacgttac   300
         N   G   K   L   I   A   Y   P   I   A   V   E   A   L   S   L   I   Y   N   K
 301     aacggcaagctgattgcttacccgatcgctgttgaagcgttatcgctgatttataacaaa   360
         D   L   L   P   N   P   P   K   T   W   E   E   I   P   A   L   D   K   E   L
 361     gatctgctgccgaacccgccaaaaacctgggaagagatcccggcgctggataaagaactg   420
         K   A   K   G   K   S   A   L   M   F   N   L   Q   E   P   Y   F   T   W   P
 421     aaagcgaaaggtaagagcgcgctgatgttcaacctgcaagaaccgtacttcacctggccg   480
         L   I   A   A   D   G   G   Y   A   F   K   Y   E   N   G   K   Y   D   I   K
 481     ctgattgctgctgacggggttatgcgttcaagtatgaaaacggcaagtacgacattaaa   540
         D   V   G   V   D   N   A   G   A   K   A   G   L   T   F   L   V   D   L   I
 541     gacgtgggcgtggataacgctggcgcgaaagcgggtctgaccttcctggttgacctgatt   600
         K   N   K   H   M   N   A   D   T   D   Y   S   I   A   E   A   A   F   N   K
 601     aaaaacaaacacatgaatgcagacaccgattactccatcgcagaagctgcctttaataaa   660
         G   E   T   A   M   T   I   N   G   P   W   A   W   S   N   I   D   T   S   K
 661     ggcgaaacagcgatgaccatcaacggcccgtgggcatggtccaacatcgacaccagcaaa   720
         V   N   Y   G   V   T   V   L   P   T   F   K   G   Q   P   S   K   P   F   V
 721     gtgaattatggtgtaacggtactgccgaccttcaagggtcaaccatccaaaccgttcgtt   780
         G   V   L   S   A   G   I   N   A   A   S   P   N   K   E   L   A   K   E   F
 781     ggcgtgctgagcgcaggtattaacgccgccagtccgaacaaagagctggcaaaagagttc   840
         L   E   N   Y   L   L   T   D   E   G   L   E   A   V   N   K   D   K   P   L
 841     ctcgaaaactatctgctgactgatgaaggtctggaagcggttaataaagacaaaccgctg   900
         G   A   V   A   L   K   S   Y   E   E   E   L   A   K   D   P   R   I   A   A
 901     ggtgccgtagcgctgaagtcttacgaggaagagttggcgaaagatccacgtattgccgcc   960
         T   M   E   N   A   Q   K   G   E   I   M   P   N   I   P   Q   M   S   A   F
 961     actatggaaaacgcccagaaaggtgaaatcatgccgaacatcccgcagatgtccgctttc  1020
         W   Y   A   V   R   T   A   V   I   N   A   A   S   G   R   Q   T   V   D   E
1021     tggtatgccgtgcgtactgcggtgatcaacgccgccagcggtcgtcagactgtcgatgaa  1080
         A   L   K   D   A   Q   T   N   S   S   S   N   N   N   N   N   N   N   N   N
1081     gccctgaaagacgcgcagactaattcgagctcgaacaacaacaacaataacaataacaac  1140
         N   L   G   I   E   G   R   G   L   E   Y   G   R   K   K   R   R   Q   R   R
1141     aacctcgggatcgagggaaggggctcgagtacggccgcaagaaacgccgccagcgccgc   1200
         R   E   F   M   S   L   L   C   R   N   K   G   C   G   Q   H   F   D   P   N
1201     cgcgaattcatgtctctactctgtcgtaacaaaggctgtgggcagcactttgacccaat  1260
         T   N   L   P   D   S   C   C   H   H   P   G   V   P   I   F   H   D   A   L
1261     accaaccttcctgattcctgttgccatcaccctggggtcccaatcttccatgatgcactt  1320
         K   G   W   S   C   C   R   K   R   T   V   D   F   S   E   F   L   N   I   K
1321     aagggttggtcctgctgccgaaagcgaactgtagatttctctgagttcttaaacatcaag  1380
         G   C   T   M   G   P   H   C   A   E   K   L   P   E   A   P   Q   P   E   G
1381     ggctgtactatgggaccacactgtgctgagaagcttcctgaggccccctcaacctgaaggc  1440
         P   A   T   S   S   S   L   Q   E   Q   K   P   L   N   V   I   P   K   S   A
1441     cctgctacaagcagttcacttcaggagcaaaaacctctgaatgtgattccaaagtcagca  1500
         E   T   L   R   R   E   R   P   K   S   E   L   P   L   K   L   L   P   L   N
1501     gagaccttgcgccgggagaggcccaagtcagagttgcctctgaagctgctgccgctaaat  1560
         I   S   Q   A   L   E   M   A   L   E   Q   K   E   L   D   Q   E   P   G   A
1561     atatcccaagccctggaaatggcattggaacagaaggaattagaccaggaacctggggca  1620
         G   L   D   S   L   I   R   T   G   S   S   C   Q   N   P   G   C   D   A   V
```

Figure 1B

```
1621  ggacttgacagtctgatccggactggttccagctgccagaacccaggatgtgatgctgtt  1680
       Y  Q  G  P  E  S  D  A  T  P  C  T  Y  H  P  G  A  P  R  F
1681  taccaaggccctgagagtgatgctactccatgtacctaccacccaggagcaccccgattc  1740
       H  E  G  M  K  S  W  S  C  C  G  I  Q  T  L  D  F  G  A  F
1741  catgagggatgaagtcttggagctgttgtggcatccagaccctggattttggggcattc   1800
       L  A  Q  P  G  C  R  V  G  R  H  D  W  G  K  Q  L  P  A  S
1801  ttggcacaaccagggtgcagagtcggtagacatgactgggggaagcagctcccagcatct  1860
       C  R  H  D  W  H  Q  T  D  S  L  V  V  V  T  V  Y  G  Q  I
1861  tgccgccatgattggcaccagacagattccttagtagtggtgactgtatatggccagatt  1920
       P  L  P  A  F  N  W  V  K  A  S  Q  T  E  L  H  V  H  I  V
1921  ccacttcctgcgtttaactgggtgaaggccagtcaaactgagcttcatgtccacattgtc  1980
       F  D  G  N  R  V  F  Q  A  Q  M  K  L  W  G  V  I  N  V  E
1981  tttgatggtaaccgtgtgttccaagcacagatgaagctctgggggtcataaacgtggag   2040
       Q  S  S  V  F  L  M  P  S  R  V  E  I  S  L  V  K  A  D  P
2041  cagagctctgtcttcttgatgccatctcgggttgaaatctccctggtcaaggctgaccca  2100
       G  S  W  A  Q  L  E  H  P  D  A  L  A  K  K  A  R  A  G  V
2101  ggatcctgggcccagctggagcaccctgatgcactagctaagaaggctagggcagggggtt  2160
       V  L  E  M  D  E  E  S  D  D  S  D  D  D  L  S  W  T  E
2161  gtgttagagatggatgaggaagaatctgacgattcagatgatgatctgagctggacagag  2220
       E  E  E  E  E  A  M  G  E  *  *
2221  gaggaggaagaggaggaagcaatgggggaatagtga
```

Figure 1C

MBP-MELUSIN-TAT

```
         M   K   I   E   E   G   K   L   V   I   W   I   N   G   D   K   G   Y   N   G
  1      atgaaaatcgaagaaggtaaactggtaatctggattaacggcgataaaggctataacggt      60
         L   A   E   V   G   K   K   F   E   K   D   T   G   I   K   V   T   V   E   H
 61      ctcgctgaagtcggtaagaaattcgagaaagataccggaattaaagtcaccgttgagcat     120
         P   D   K   L   E   E   K   F   P   Q   V   A   A   T   G   D   G   P   D   I
121      ccggataaactggaagagaaattcccacaggttgcggcaactggcgatggccctgacatt     180
         I   F   W   A   H   D   R   F   G   G   Y   A   Q   S   G   L   L   A   E   I
181      atcttctgggcacacgaccgctttggtggctacgctcaatctggcctgttggctgaaatc     240
         T   P   D   K   A   F   Q   D   K   L   Y   P   F   T   W   D   A   V   R   Y
241      accccggacaaagcgttccaggacaagctgtatccgtttacctgggatgccgtacgttac     300
         N   G   K   L   I   A   Y   P   I   A   V   E   A   L   S   L   I   Y   N   K
301      aacggcaagctgattgcttacccgatcgctgttgaagcgttatcgctgatttataacaaa     360
         D   L   L   P   N   P   P   K   T   W   E   E   I   P   A   L   D   K   E   L
361      gatctgctgccgaacccgccaaaaaacctgggaagagatcccggcgctggataaagaactg     420
         K   A   K   G   K   S   A   L   M   F   N   L   Q   E   P   Y   F   T   W   P
421      aaagcgaaaggtaagagcgcgctgatgttcaacctgcaagaaccgtacttcacctggccg     480
         L   I   A   A   D   G   G   Y   A   F   K   Y   E   N   G   K   Y   D   I   K
481      ctgattgctgctgacgggggttatgcgttcaagtatgaaaacggcaagtacgacattaaa     540
         D   V   G   V   D   N   A   G   A   K   A   G   L   T   F   L   V   D   L   I
541      gacgtgggcgtggataacgctggcgcgaaagcgggtctgaccttcctggttgacctgatt     600
         K   N   K   H   M   N   A   D   T   D   Y   S   I   A   E   A   A   F   N   K
601      aaaaacaaacacatgaatgcagacaccgattactccatcgcagaagctgcctttaataaa     660
         G   E   T   A   M   T   I   N   G   P   W   A   W   S   N   I   D   T   S   K
661      ggcgaaacagcgatgaccatcaacggcccgtgggcatggtccaacatcgacaccagcaaa     720
         V   N   Y   G   V   T   V   L   P   T   F   K   G   Q   P   S   K   P   F   V
721      gtgaattatggtgtaacggtactgccgaccttcaagggtcaaccatccaaaccgttcgtt     780
         G   V   L   S   A   G   I   N   A   A   S   P   N   K   E   L   A   K   E   F
781      ggcgtgctgagcgcaggtattaacgccgccagtccgaacaaagagctggcaaaagagttc     840
         L   E   N   Y   L   L   T   D   E   G   L   E   A   V   N   K   D   K   P   L
841      ctcgaaaactatctgctgactgatgaaggtctggaagcggttaataaagacaaaccgctg     900
```

Figure 1D

```
              G   A   V   A   L   K   S   Y   E   E   E   L   A   K   D   P   R   I   A   A
 901    ggtgccgtagcgctgaagtcttacgaggaagagttggcgaaagatccacgtattgccgcc    960
          T   M   E   N   A   Q   K   G   E   I   M   P   N   I   P   Q   M   S   A   F
 961    actatggaaaacgcccagaaaggtgaaatcatgccgaacatcccgcagatgtccgctttc   1020
          W   Y   A   V   R   T   A   V   I   N   A   A   S   G   R   Q   T   V   D   E
1021    tggtatgccgtgcgtactgcggtgatcaacgccgccagcggtcgtcagactgtcgatgaa   1080
          A   L   K   D   A   Q   T   N   S   S   S   N   N   N   N   N   N   N   N   N
1081    gccctgaaagacgcgcagactaattcgagctcgaacaacaacaacaataacaataacaac   1140
          N   L   G   I   E   G   R   G   E   N   L   Y   F   Q   G   E   F   M   S   L
1141    aacctcgggatcgagggaaggggggaaaacctgtacttccagggggaattcatgtctcta   1200
          L   C   R   N   K   G   C   G   Q   H   F   D   P   N   T   N   L   P   D   S
1201    ctctgtcgtaacaaaggctgtgggcagcactttgaccctaataccaaccttcctgattcc   1260
          C   C   H   H   P   G   V   P   I   F   H   D   A   L   K   G   W   S   C   C
1261    tgttgccatcaccctggggtcccaatcttccatgatgcacttaagggttggtcctgctgc   1320
          R   K   R   T   V   D   F   S   E   F   L   N   I   K   G   C   T   M   G   P
1321    cgaaagcgaactgtagatttctctgagttcttaaacatcaagggctgtactatgggacca   1380
          H   C   A   E   K   L   P   E   A   P   Q   P   E   G   P   A   T   S   S   S
1381    cactgtgctgagaagcttcctgaggcccctcaacctgaaggccctgctacaagcagttca   1440
          L   Q   E   Q   K   P   L   N   V   I   P   K   S   A   E   T   L   R   R   E
1441    cttcaggagcaaaaacctctgaatgtgattccaaagtcagcagagaccttgcgccgggag   1500
          R   P   K   S   E   L   P   L   K   L   L   P   L   N   I   S   Q   A   L   E
1501    aggcccaagtcagagttgcctctgaagctgctgccgctaaatatatcccaagccctggaa   1560
          M   A   L   E   Q   K   E   L   D   Q   E   P   G   A   G   L   D   S   L   I
1561    atggcattggaacagaaggaattagaccaggaacctggggcaggacttgacagtctgatc   1620
          R   T   G   S   S   C   Q   N   P   G   C   D   A   V   Y   Q   G   P   E   S
1621    cggactggttccagctgccagaacccaggatgtgatgctgtttaccaaggccctgagagt   1680
          D   A   T   P   C   T   Y   H   P   G   A   P   R   F   H   E   G   M   K   S
1681    gatgctactccatgtacctaccacccaggagcaccccgattccatgagggggatgaagtct   1740
          W   S   C   C   G   I   Q   T   L   D   F   G   A   F   L   A   Q   P   G   C
1741    tggagctgttgtggcatccagaccctggattttggggcattcttggcacaaccagggtgc   1800
          R   V   G   R   H   D   W   G   K   Q   L   P   A   S   C   R   H   D   W   H
1801    agagtcggtagacatgactgggggaagcagctcccagcatcttgccgccatgattggcac   1860
          Q   T   D   S   L   V   V   T   V   Y   G   Q   I   P   L   P   A   F   N
1861    cagacagattccttagtagtggtgactgtatatgggcagattccacttcctgcgtttaac   1920
          W   V   K   A   S   Q   T   E   L   H   V   H   I   V   F   D   G   N   R   V
1921    tgggtgaaggccagtcaaactgagcttcatgtccacattgtctttgatggtaaccgtgtg   1980
          F   Q   A   Q   M   K   L   W   G   V   I   N   V   E   Q   S   S   V   F   L
1981    ttccaagcacagatgaagctctgggggtcataaacgtggagcagagctctgtcttcttg   2040
          M   P   S   R   V   E   I   S   L   V   K   A   D   P   G   S   W   A   Q   L
2041    atgccatctcgggttgaaatctccctggtcaaggctgacccaggatcctgggcccagctg   2100
          E   H   P   D   A   L   A   K   K   A   R   A   G   V   V   L   E   M   D   E
2101    gagcaccctgatgcactagctaagaaggctagggcaggggttgtgttagagatggatgag   2160
          E   E   S   D   D   S   D   D   D   L   S   W   T   E   E   E   E   E   E   E
2161    gaagaatctgacgattcagatgatgatctgagctggacagaggaggaggaagaggaggaa   2220
          A   M   G   E   Y   G   R   K   K   R   R   Q   R   R   R   *
2221    gcaatggggggaatacggccgcaagaaacgccgccagcgccgccgctag
```

MBP-TAT-melusin

```
    Smal   Xhol                 TAT                    EcoRI
5'-tccccc ggg ctc gag tac ggc cgc aag aaa cgc cgc cag cgc cgc cgc gaa ttcggg-3'
               Y   G   R   K   K   R   R   Q   R   R   R
```

Figure 1F

MBP-melusin-TAT

A

Kinetic data from Rat1 I.V. curve:

| | |
|---|---:|
| CL | 1 |
| MRT | 67.68 |
| Vss | 67 |
| Terminal K | 7.12E-03 |
| Terminal T1/2 | 97.36 |
| CP estimated at longest time | 129.79 |
| Tmax | 0.00E+00 |
| Cmax | 88900.94 |
| AUC to Tlast | 2.62E+06 |
| Tlast | 480.00 |
| AUC extrap to time infinity | 2.64E+06 |
| Percent extrapolated AUC | .69 |
| AUMC | 1.79E+08 |
| Percent extrapolated AUMC | 6.33 |

B

C

Extrapolated Terminal T1/2 = 120 min

Figure 3/cont.
D
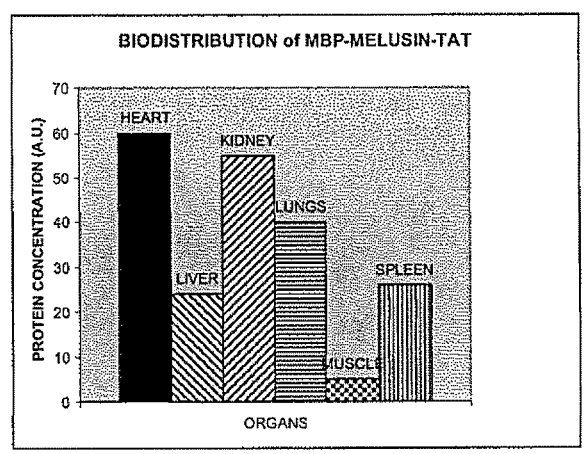
E
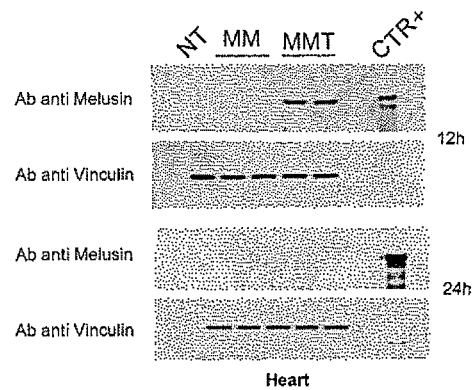

Figure 6

| Cell penetrating polypeptides | Sequence | SEQ ID No. |
|---|---|---|
| HIV TAT peptide | YGRKKRRQRRR | 11 |
| Penetratin (pAntp) | RQIKIWFQNRRMKWKK | 12 |
| R7 peptide | RRRRRRR | 13 |
| KALA peptide | WEAKLAKALAKALAKHLAKALAKALKACEA | 14 |
| Buforin 2 | TRSSRAGLQFPVGRVHRLLRK | 15 |
| MAP | KLALKLALKALKAALKLA-amide | 16 |
| Transportan | GWTLNSAGYLLGKINLKALAALAKKIL-amide | 17 |
| Transportan 10 | AGYLLGKINLKALAALAKKIL-amide | 18 |
| pVEC | LLIILRRRIRKQAHAHSK-amide | 19 |
| MPG peptide | GALFLGWLGAAGSTMGAPKKKRKV-amide | 20 |

SEQUENCE LISTING

<160> NUMBER OF SEQ ID NOS: 20

<210> SEQ ID NO 1
<211> LENGTH: 1041
<212> TYPE: DNA
<213> ORGANISM: homo sapiens

<400> SEQUENCE: 1

```
atgtctctac tctgtcgtaa caaaggctgt gggcagcact ttgaccctaa taccaacctt      60
cctgattcct gttgccatca ccctggggtc ccaatcttcc atgatgcact taagggttgg     120
tcctgctgcc gaaagcgaac tgtagatttc tctgagttct taaacatcaa gggctgtact     180
atgggaccac actgtgctga gaagcttcct gaggcccctc aacctgaagg ccctgctaca     240
agcagttcac ttcaggagca aaaacctctg aatgtgattc caaagtcagc agagaccttg     300
cgccgggaga ggcccaagtc agagttgcct ctgaagctgc tgccgctaaa tatatcccaa     360
gccctggaaa tggcattgga acagaaggaa ttagaccagg aacctggggc aggacttgac     420
agtctgatcc ggactggttc cagctgccag aacccaggat gtgatgctgt ttaccaaggc     480
cctgagagtg atgctactcc atgtacctac cacccaggag caccccgatt ccatgagggg     540
atgaagtctt ggagctgttg tggcatccag accctggatt ttggggcatt cttggcacaa     600
ccagggtgca gagtcggtag acatgactgg gggaagcagc tcccagcatc ttgccgccat     660
gattggcacc agacagattc cttagtagtg gtgactgtat atggccagat tccacttcct     720
gcgtttaact gggtgaaggc cagtcaaact gagcttcatg tccacattgt ctttgatggt     780
aaccgtgtgt tccaagcaca gatgaagctc tgggggtca taaacgtgga gcagagctct     840
gtcttcttga tgccatctcg ggttgaaatc tccctggtca aggctgaccc aggatcctgg     900
gcccagctgg agcaccctga tgcactagct aagaaggcta gggcagggt tgtgttagag     960
atggatgagg aagaatctga cgattcagat gatgatctga gctggacaga ggaggaggaa    1020
gaggaggaag caatgggggga a                                              1041
```

<210> SEQ ID NO 2
<211> LENGTH: 33
<212> TYPE: DNA
<213> ORGANISM: artificial
<220> FEATURE:
<223> OTHER INFORMATION: oligonucleotide from HIV virus TAT protein

<400> SEQUENCE: 2

```
tacggccgca agaaacgccg ccagcgccgc cgc                                    33
```

<210> SEQ ID NO 3
<211> LENGTH: 11
<212> TYPE: PRT
<213> ORGANISM: artificial
<220> FEATURE:
<223> OTHER INFORMATION: oligopeptide coded by oligonucleotide sequence
      of HIV virus TAT protein

<400> SEQUENCE: 3

Tyr Gly Arg Lys Lys Arg Arg Gln Arg Arg Arg
1               5                   10

<210> SEQ ID NO 4
<211> LENGTH: 21
<212> TYPE: DNA
<213> ORGANISM: artificial
<220> FEATURE:

```
<223> OTHER INFORMATION: oligonucleotide coding for the cleavage site of
      TEV protease

<400> SEQUENCE: 4
gaaaacctgt acttccaggg g                                              21

<210> SEQ ID NO 5
<211> LENGTH: 7
<212> TYPE: PRT
<213> ORGANISM: artificial
<220> FEATURE:
<223> OTHER INFORMATION: oligopeptide 1 coded by oligonucleotide coding
      cleavage site of TEV protease

<400> SEQUENCE: 5

Glu Asn Leu Tyr Phe Gln Gly
1               5

<210> SEQ ID NO 6
<211> LENGTH: 1161
<212> TYPE: DNA
<213> ORGANISM: artificial
<220> FEATURE:
<223> OTHER INFORMATION: maltose binding protein coding sequence

<400> SEQUENCE: 6
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt atcgctgat ttataacaaa      360 gatctgctgc cgaacccgcc aaaaacctgg gaagagatcc cggcgctgga taaagaactg     420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc      960 actatggaaa acgcccagaa aggtgaaatc atgccgaaca tcccgcagat gtccgctttc     1020
tggtatgccg tgcgtactgc ggtgatcaac gccgccagcg tcgtcagac tgtcgatgaa     1080 gccctgaaag acgcgcagac taattcgagc tcgaacaaca caacaataa caataacaac     1140 aacctcggga tcgagggaag g                                              1161

<210> SEQ ID NO 7
<211> LENGTH: 2256
<212> TYPE: DNA
<213> ORGANISM: artificial
<220> FEATURE:
<223> OTHER INFORMATION: MBP-TAT-MELUSIN

<400> SEQUENCE: 7
```

-continued

```
atgaaaatcg aagaaggtaa actggtaatc tggattaacg gcgataaagg ctataacggt    60
ctcgctgaag tcggtaagaa attcgagaaa gataccggaa ttaaagtcac cgttgagcat   120
ccggataaac tggaagagaa attcccacag gttgcggcaa ctggcgatgg ccctgacatt   180
atcttctggg cacacgaccg ctttggtggc tacgctcaat ctggcctgtt ggctgaaatc   240
accccggaca aagcgttcca ggacaagctg tatccgttta cctgggatgc cgtacgttac   300
aacggcaagc tgattgctta cccgatcgct gttgaagcgt tatcgctgat ttataacaaa   360
gatctgctgc cgaacccgcc aaaaacctgg gaagagatcc cggcgctgga taagaactg    420
aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtgggcg tggataacgc tggcgcgaaa gcgggtctga ccttcctggt tgacctgatt   600
aaaaacaaac acatgaatgc agacaccgat tactccatcg cagaagctgc ctttaataaa   660
ggcgaaacag cgatgaccat caacggcccg tgggcatggt ccaacatcga caccagcaaa   720
gtgaattatg tgtaacggt actgccgacc ttcaagggtc aaccatccaa accgttcgtt   780
ggcgtgctga gcgcaggtat taacgccgcc agtccgaaca aagagctggc aaaagagttc   840
ctcgaaaact atctgctgac tgatgaaggt ctggaagcgg ttaataaaga caaaccgctg   900
ggtgccgtag cgctgaagtc ttacgaggaa gagttggcga agatccacg tattgccgcc   960
actatggaaa acgcccagaa aggtgaaatc atgccgaaca tcccgcagat gtccgctttc  1020
tggtatgccg tgcgtactgc ggtgatcaac gccgccagcg tcgtcagac tgtcgatgaa  1080
gccctgaaag acgcgcagac taattcgagc tcgaacaaca acaacaataa caataacaac  1140
aacctcggga tcgagggaag ggggctcgag tacggccgca agaaacgccg ccagcgccgc  1200
cgcgaattca tgtctctact ctgtcgtaac aaaggctgtg ggcagcactt tgaccctaat  1260
accaaccttc ctgattcctg ttgccatcac cctggggtcc caatcttcca tgatgcactt  1320
aagggttggt cctgctgccg aaagcgaact gtagatttct ctgagttctt aaacatcaag  1380
ggctgtacta tgggaccaca ctgtgctgag aagcttcctg aggcccctca acctgaaggc  1440
cctgctacaa gcagttcact tcaggagcaa aaacctctga atgtgattcc aaagtcagca  1500
gagaccttgc gccgggagag gcccaagtca gagttgcctc tgaagctgct gccgctaaat  1560
atatcccaag ccctggaaat ggcattggaa cagaaggaat tagaccagga acctggggca  1620
ggacttgaca gtctgatccg gactggttcc agctgccaga acccaggatg tgatgctgtt  1680
taccaaggcc ctgagagtga tgctactcca tgtacctacc acccaggagc accccgattc  1740
catgagggga tgaagtcttg gagctgttgt ggcatccaga ccctggattt tggggcattc  1800
ttggcacaac cagggtgcag agtcggtaga catgactggg ggaagcagct cccagcatct  1860
tgccgccatg attggcacca gacagattcc ttagtagtgg tgactgtata tggccagatt  1920
ccacttcctg cgtttaactg ggtgaaggcc agtcaaactg agcttcatgt ccacattgtc  1980
tttgatggta accgtgtgtt ccaagcacag atgaagctct gggggtcat aaacgtggag  2040
cagagctctg tcttcttgat gccatctcgg gttgaaatct ccctggtcaa ggctgaccca  2100
ggatcctggg cccagctgga gcaccctgat gcactagcta agaaggctag gcaggggtt   2160
gtgttagaga tggatgagga agaatctgac gattcagatg atgatctgag ctggacagag  2220
gaggaggaag aggaggaagc aatgggggaa tagtga                            2256
```

<210> SEQ ID NO 8
<211> LENGTH: 750

```
<212> TYPE: PRT
<213> ORGANISM: artificial
<220> FEATURE:
<223> OTHER INFORMATION: MBP-TAT-MELUSIN aminoacidic sequence

<400> SEQUENCE: 8

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Gly Leu Glu Tyr Gly Arg Lys Lys Arg Arg Gln Arg Arg
```

```
                385                 390                 395                 400
Arg Glu Phe Met Ser Leu Leu Cys Arg Asn Lys Gly Cys Gly Gln His
                    405                 410                 415
Phe Asp Pro Asn Thr Asn Leu Pro Asp Ser Cys Cys His His Pro Gly
                420                 425                 430
Val Pro Ile Phe His Asp Ala Leu Lys Gly Trp Ser Cys Cys Arg Lys
            435                 440                 445
Arg Thr Val Asp Phe Ser Glu Phe Leu Asn Ile Lys Gly Cys Thr Met
        450                 455                 460
Gly Pro His Cys Ala Glu Lys Leu Pro Glu Ala Pro Gln Pro Glu Gly
465                 470                 475                 480
Pro Ala Thr Ser Ser Leu Gln Glu Gln Lys Pro Leu Asn Val Ile
                485                 490                 495
Pro Lys Ser Ala Glu Thr Leu Arg Arg Glu Arg Pro Lys Ser Glu Leu
                500                 505                 510
Pro Leu Lys Leu Leu Pro Leu Asn Ile Ser Gln Ala Leu Glu Met Ala
                515                 520                 525
Leu Glu Gln Lys Glu Leu Asp Gln Pro Gly Ala Gly Leu Asp Ser
530                 535                 540
Leu Ile Arg Thr Gly Ser Ser Cys Gln Asn Pro Gly Cys Asp Ala Val
545                 550                 555                 560
Tyr Gln Gly Pro Glu Ser Asp Ala Thr Pro Cys Thr Tyr His Pro Gly
                565                 570                 575
Ala Pro Arg Phe His Glu Gly Met Lys Ser Trp Ser Cys Cys Gly Ile
                580                 585                 590
Gln Thr Leu Asp Phe Gly Ala Phe Leu Ala Gln Pro Gly Cys Arg Val
                595                 600                 605
Gly Arg His Asp Trp Gly Lys Gln Leu Pro Ala Ser Cys Arg His Asp
                610                 615                 620
Trp His Gln Thr Asp Ser Leu Val Val Thr Val Tyr Gly Gln Ile
625                 630                 635                 640
Pro Leu Pro Ala Phe Asn Trp Val Lys Ala Ser Gln Thr Glu Leu His
                645                 650                 655
Val His Ile Val Phe Asp Gly Asn Arg Val Phe Gln Ala Gln Met Lys
                660                 665                 670
Leu Trp Gly Val Ile Asn Val Glu Gln Ser Ser Val Phe Leu Met Pro
                675                 680                 685
Ser Arg Val Glu Ile Ser Leu Val Lys Ala Asp Pro Gly Ser Trp Ala
                690                 695                 700
Gln Leu Glu His Pro Asp Ala Leu Ala Lys Lys Ala Arg Ala Gly Val
705                 710                 715                 720
Val Leu Glu Met Asp Glu Glu Glu Ser Asp Asp Ser Asp Asp Asp Leu
                    725                 730                 735
Ser Trp Thr Glu Glu Glu Glu Glu Glu Ala Met Gly Glu
                    740                 745                 750

<210> SEQ ID NO 9
<211> LENGTH: 2268
<212> TYPE: DNA
<213> ORGANISM: artificial
<220> FEATURE:
<223> OTHER INFORMATION: MBP-MELUSIN-TAT construct

<400> SEQUENCE: 9
atgaaaatcg aagaaggtaa actggtaatc tggattaacg gcgataaagg ctataacggt        60
```

```
ctcgctgaag tcggtaagaa attcgagaaa gataccggaa ttaaagtcac cgttgagcat    120
ccggataaac tggaagagaa attcccacag gttgcggcaa ctggcgatgg ccctgacatt    180
atcttctggg cacacgaccg ctttggtggc tacgctcaat ctggcctgtt ggctgaaatc    240
accccggaca aagcgttcca ggacaagctg tatccgttta cctgggatgc cgtacgttac    300
aacggcaagc tgattgctta cccgatcgct gttgaagcgt tatcgctgat ttataacaaa    360
gatctgctgc cgaacccgcc aaaaacctgg gaagagatcc cggcgctgga taagaactg     420
aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540
gacgtgggcg tggataacgc tggcgcgaaa gcgggtctga ccttcctggt tgacctgatt    600
aaaaacaaac acatgaatgc agacaccgat tactccatcg cagaagctgc ctttaataaa    660
ggcgaaacag cgatgaccat caacggcccg tgggcatggt ccaacatcga caccagcaaa    720
gtgaattatg gtgtaacggt actgccgacc ttcaagggtc aaccatccaa accgttcgtt    780
ggcgtgctga gcgcaggtat taacgccgcc agtccgaaca aagagctggc aaaagagttc    840
ctcgaaaact atctgctgac tgatgaaggt ctggaagcgg ttaataaaga caaaccgctg    900
ggtgccgtag cgctgaagtc ttacgaggaa gagttggcga agatccacg tattgccgcc    960
actatggaaa cgcccagaa aggtgaaatc atgccgaaca tcccgcagat gtccgctttc    1020
tggtatgccg tgcgtactgc ggtgatcaac gccgccagcg gtcgtcagac tgtcgatgaa    1080
gccctgaaag acgcgcagac taattcgagc tcaacaaca caacaataa caataacaac    1140
aacctcggga tcgagggaag gggggaaaac ctgtacttcc aggggaatt catgtctcta    1200
ctctgtcgta acaaaggctg tgggcagcac tttgaccca ataccaacct tcctgattcc    1260
tgttgccatc accctggggt cccaatcttc catgatgcac ttaagggttg gtcctgctgc    1320
cgaaagcgaa ctgtagattt ctctgagttc ttaaacatca agggctgtac tatgggacca    1380
cactgtgctg agaagcttcc tgaggcccct caacctgaag gccctgctac aagcagttca    1440
cttcaggagc aaaaacctct gaatgtgatt ccaaagtcag cagagacctt gcgccgggag    1500
aggcccaagt cagagttgcc tctgaagctg ctgccgctaa atatatccca agccctggaa    1560
atggcattgg aacagaagga attagaccag gaacctgggg caggacttga cagtctgatc    1620
cggactggtt ccagctgcca gaacccagga tgtgatgctg tttaccaagg ccctgagagt    1680
gatgctactc catgtaccta ccacccagga gcaccccgat tccatgaggg gatgaagtct    1740
tggagctgtt gtggcatcca gaccctggat tttggggcat tcttggcaca accagggtgc    1800
agagtcggta gacatgactg ggggaagcag ctcccagcat cttgccgcca tgattggcac    1860
cagacagatt cctagtagt ggtgactgta tatggccaga ttccacttcc tgcgtttaac    1920
tgggtgaagg ccagtcaaac tgagcttcat gtccacattg tctttgatgg taaccgtgtg    1980
ttccaagcac agatgaagct ctgggggtc ataaacgtgg agcagagctc tgtcttcttg    2040
atgccatctc gggttgaaat ctccctggtc aaggctgacc caggatcctg ggcccagctg    2100
gagcaccctg atgcactagc taagaaggct agggcaggg ttgtgttaga gatggatgag    2160
gaagaatctg acgattcaga tgatgatctg agctggacag aggaggagga agaggaggaa    2220
gcaatggggg aatacggccg caagaaacgc cgccagcgcc gccgctag                 2268
```

<210> SEQ ID NO 10
<211> LENGTH: 755
<212> TYPE: PRT
<213> ORGANISM: artificial
<220> FEATURE:

<223> OTHER INFORMATION: MBP-MELUSIN-TAT aminoacidic sequence

<400> SEQUENCE: 10

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
        370                 375                 380

Glu Gly Arg Gly Glu Asn Leu Tyr Phe Gln Gly Glu Phe Met Ser Leu
385                 390                 395                 400

Leu Cys Arg Asn Lys Gly Cys Gly Gln His Phe Asp Pro Asn Thr Asn
```

```
                      405                 410                 415
Leu Pro Asp Ser Cys Cys His His Pro Gly Val Pro Ile Phe His Asp
            420                 425                 430
Ala Leu Lys Gly Trp Ser Cys Cys Arg Lys Arg Thr Val Asp Phe Ser
            435                 440                 445
Glu Phe Leu Asn Ile Lys Gly Cys Thr Met Gly Pro His Cys Ala Glu
            450                 455                 460
Lys Leu Pro Glu Ala Pro Gln Pro Glu Gly Pro Ala Thr Ser Ser Ser
465                 470                 475                 480
Leu Gln Glu Gln Lys Pro Leu Asn Val Ile Pro Lys Ser Ala Glu Thr
            485                 490                 495
Leu Arg Arg Glu Arg Pro Lys Ser Glu Leu Pro Leu Lys Leu Leu Pro
            500                 505                 510
Leu Asn Ile Ser Gln Ala Leu Glu Met Ala Leu Glu Gln Lys Glu Leu
            515                 520                 525
Asp Gln Glu Pro Gly Ala Gly Leu Asp Ser Leu Ile Arg Thr Gly Ser
            530                 535                 540
Ser Cys Gln Asn Pro Gly Cys Asp Ala Val Tyr Gln Gly Pro Glu Ser
545                 550                 555                 560
Asp Ala Thr Pro Cys Thr Tyr His Pro Gly Ala Pro Arg Phe His Glu
            565                 570                 575
Gly Met Lys Ser Trp Ser Cys Cys Gly Ile Gln Thr Leu Asp Phe Gly
            580                 585                 590
Ala Phe Leu Ala Gln Pro Gly Cys Arg Val Gly Arg His Asp Trp Gly
            595                 600                 605
Lys Gln Leu Pro Ala Ser Cys Arg His Asp Trp His Gln Thr Asp Ser
            610                 615                 620
Leu Val Val Val Thr Val Tyr Gly Gln Ile Pro Leu Pro Ala Phe Asn
625                 630                 635                 640
Trp Val Lys Ala Ser Gln Thr Glu Leu His Val His Ile Val Phe Asp
            645                 650                 655
Gly Asn Arg Val Phe Gln Ala Gln Met Lys Leu Trp Gly Val Ile Asn
            660                 665                 670
Val Glu Gln Ser Ser Val Phe Leu Met Pro Ser Arg Val Glu Ile Ser
            675                 680                 685
Leu Val Lys Ala Asp Pro Gly Ser Trp Ala Gln Leu Glu His Pro Asp
            690                 695                 700
Ala Leu Ala Lys Lys Ala Arg Ala Gly Val Val Leu Glu Met Asp Glu
705                 710                 715                 720
Glu Glu Ser Asp Asp Ser Asp Asp Leu Ser Trp Thr Glu Glu
            725                 730                 735
Glu Glu Glu Glu Ala Met Gly Glu Tyr Gly Arg Lys Lys Arg Arg Gln
            740                 745                 750
Arg Arg Arg
        755

<210> SEQ ID NO 11
<211> LENGTH: 11
<212> TYPE: PRT
<213> ORGANISM: artificial
<220> FEATURE:
<223> OTHER INFORMATION: HIV TAT peptide

<400> SEQUENCE: 11

Tyr Gly Arg Lys Lys Arg Arg Gln Arg Arg
1               5                   10
```

```
<210> SEQ ID NO 12
<211> LENGTH: 16
<212> TYPE: PRT
<213> ORGANISM: artificial
<220> FEATURE:
<223> OTHER INFORMATION: Penetratin (pAntp)

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 7
<212> TYPE: PRT
<213> ORGANISM: artificial
<220> FEATURE:
<223> OTHER INFORMATION: R7 peptide

<400> SEQUENCE: 13

Arg Arg Arg Arg Arg Arg Arg
1               5

<210> SEQ ID NO 14
<211> LENGTH: 30
<212> TYPE: PRT
<213> ORGANISM: artificial
<220> FEATURE:
<223> OTHER INFORMATION: KALA peptide

<400> SEQUENCE: 14

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 15
<211> LENGTH: 21
<212> TYPE: PRT
<213> ORGANISM: artificial
<220> FEATURE:
<223> OTHER INFORMATION: Buforin 2

<400> SEQUENCE: 15

Thr Arg Ser Ser Arg Ala Gly Leu Gln Phe Pro Val Gly Arg Val His
1               5                   10                  15

Arg Leu Leu Arg Lys
            20

<210> SEQ ID NO 16
<211> LENGTH: 18
<212> TYPE: PRT
<213> ORGANISM: artificial
<220> FEATURE:
<223> OTHER INFORMATION: MAP

<400> SEQUENCE: 16

Lys Leu Ala Leu Lys Leu Ala Leu Lys Ala Leu Lys Ala Ala Leu Lys
1               5                   10                  15

Leu Ala

<210> SEQ ID NO 17
<211> LENGTH: 27
<212> TYPE: PRT
<213> ORGANISM: artificial
<220> FEATURE:
```

```
<223> OTHER INFORMATION: Transportan

<400> SEQUENCE: 17

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 18
<211> LENGTH: 21
<212> TYPE: PRT
<213> ORGANISM: artificial
<220> FEATURE:
<223> OTHER INFORMATION: Transportan 10

<400> SEQUENCE: 18

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 19
<211> LENGTH: 18
<212> TYPE: PRT
<213> ORGANISM: artificial
<220> FEATURE:
<223> OTHER INFORMATION: pVEC

<400> SEQUENCE: 19

Leu Leu Ile Ile Leu Arg Arg Arg Ile Arg Lys Gln Ala His Ala His
1               5                   10                  15

Ser Lys

<210> SEQ ID NO 20
<211> LENGTH: 24
<212> TYPE: PRT
<213> ORGANISM: artificial
<220> FEATURE:
<223> OTHER INFORMATION: MPG peptide

<400> SEQUENCE: 20

Gly Ala Leu Phe Leu Gly Trp Leu Gly Ala Ala Gly Ser Thr Met Gly
1               5                   10                  15

Ala Pro Lys Lys Lys Arg Lys Val
            20
```

RECOMBINANT MELUSIN FUSION PROTEIN AS PHARMACOLOGICAL AGENT IN THE TREATMENT OF HEART PATHOLOGIES

FIELD OF INVENTION

The present invention concerns a recombinant form of the human protein melusin or portions thereof for the treatment of heart pathologies, such as heart failure, dilated cardiomyopathy and myocardial infarct.

BACKGROUND OF THE INVENTION

In subjects affected by cardiovascular pathologies such as aortic stenosis, chronic arterial hypertension, valvular dysfunction, myocardial infarct, myocarditis, idiopathic cardiomyopathy, is subjected to increased workload. The presence of a pathological insult induces the heart to undergo hypertrophy, a tissue remodelling program aimed at maintaining cardiac function. Although cardiac hypertrophy is, thus, initially compensatory and beneficial, under condition of chronic pathological stimuli, additional events might occur that either reduce the efficacy of the hypertrophy response or activate additional pathways causing cardiac dilation and progressively leading to heart dysfunction and failure.

Melusin functional properties can provide a highly innovative and robust approach to counteract the evolution toward heart dysfunction and failure.

Melusin, in fact, is selectively expressed in skeletal muscle fibers and cardiomyocytes (Brancaccio et al., 1999), and it is required to activate a compensatory cardiac hypertrophy program in response to stress conditions such as chronic pressure overload of the left ventricle (Brancaccio et al., 2003). Such a function requires the activation of AKT/GSK3beta and of ERK (Brancaccio et al., 2003) (De Acetis et al., 2005), two well known signaling pathways in cardiac hypertrophy.

Forced expression of melusin in heart of transgenic mice efficiently protects from left ventricle dilation and failure when heart is subjected to prolonged pressure overload (De Acetis et al., 2005).

In human patients affected by dilated cardiomyopathy in response to aortic stenosis reduction melusin expression parallels the functional cardiac impairment as measured by ejection fraction values (Brokat et al 2007).

Current leading medications for the treatment of Heart Failure (CHF) include drugs targeted to hemodynamic overload (diuretic and nitrates), to inhibit the activity of both renin-angiotensin (ACE-inhibitors and sartans) and sympathetic nervous system (beta-blockers). Although development of these drugs has led to better treatment, 50% of the patients with the most advanced stage of heart failure die within a year, the heart transplant still being the only cure. Indeed, most, if not all, available drugs are mainly aimed to reduce cardiac hemodynamic overload by reducing blood pressure and undesirable consequences of heart failure on different peripheral organs.

Thus, therapeutical approaches aimed to correct the major defects in cardiac muscle at the basis of heart failure represent a major current medical need as they should provide a much more effective outcome compared to inotropic therapy or mechanical devices assisting heart function.

SUMMARY OF THE INVENTION

Taking into account these premises, the need is therefore felt for improved solutions enabling the therapeutical treatment of heart pathologies, such as heart failure, and cardiomyopathy caused by aortic stenosis, chronic arterial hypertension, valvular dysfunction, myocardial infarct, myocarditis or, idiopathic cardiomyopathy, avoiding the above referenced disadvantages.

The object of this disclosure is providing such improved solutions.

According to the invention, the above object is achieved thanks to the subject matter recalled specifically in the ensuing claims, which are understood as forming an integral part of this disclosure.

An embodiment of the present disclosure provides a recombinant melusin fusion protein having an improved stability and an enhanced capability to reach intracellular compartments as compared to recombinant melusin in vivo, wherein said protein comprises i) a human melusin protein having the amino acid sequence as defined in SEQ ID No.:1, or a homologue thereof having at least 60%, preferably at least 80%, more preferably at least 90% sequence identity to SEQ ID No.:1 and having the function of native melusin protein or a human melusin portion derived from SEQ ID No.:1 or homologue thereof having at least 60%, preferably at least 80%, more preferably at least 90% sequence identity of the melusin portion derived from SEQ ID No.:1 and having the function of native melusin protein and ii) a cell penetrating polypeptide.

More specifically, the recombinant melusin fusion protein can include the melusin protein or portion thereof fused to a cell penetrating polypeptide selected among HIV-TAT polypeptide, polylysine, peptides from the homeodomain of antennapedia, peptides of sequences 11-20 (FIG. 6).

In a further embodiment, the recombinant melusin fusion protein can be conjugated to the N-terminus to a tag sequence, which can be selected among maltose-binding protein (MBP), glutathione S-transferase (GST), hexa Histidine peptide (HIS), Flag epitope, Myc epitope, Ig domain, staphylococcal protein A.

In a still further embodiment disclosed in the instant application, the recombinant melusin fusion protein can be used as a medicament, preferably for treatment of heart pathologies, more preferably heart failure, and cardiomyopathy caused by aortic stenosis, chronic arterial hypertension, valvular dysfunction, myocardial infarct, myocarditis or, idiopathic cardiomyopathy.

The recombinant melusin fusion protein object of the present disclosure has heart hypertrophy inducement activity in vivo.

BRIEF DESCRIPTION OF THE DRAWINGS

The invention will now be described, by way of example only, with reference to the enclosed figures of drawing, wherein:

FIG. 6: Sequences of cell penetrating polypeptides suitable for the production of recombinant melusin fusion proteins (SEQ ID NOs:11-20, respectively).

DETAILED DESCRIPTION OF THE INVENTION

Figure 1E:
(FIG. 1E—SEQ ID NOs:2 and 3, and nucleotides 1171-1203 of SEQ ID NO:7 and amino acids 391-401 of SEQ ID NO:8; nucleotides 1076-1149 of SEQ ID NO:7 and amino acids 365-383 of SEQ ID NO:8.
Figure 1E:
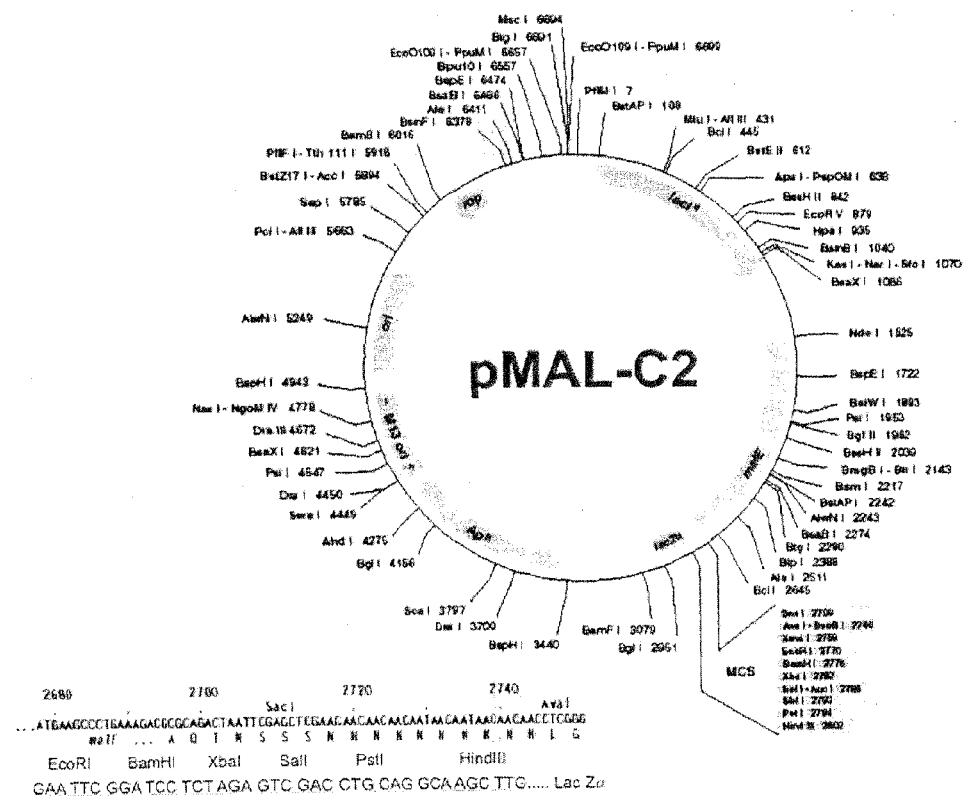
Figure 1E:
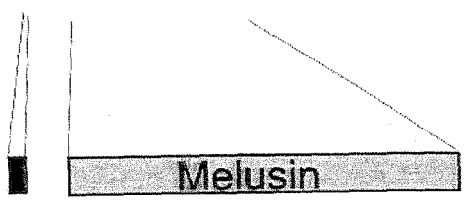
Figure 1G:
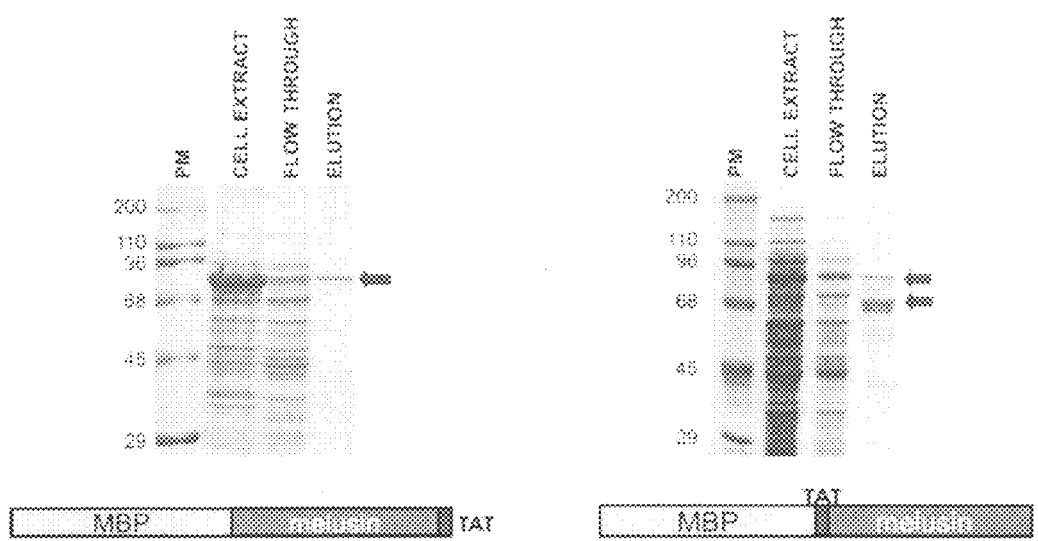
FIG. 1: Nucleotide and amino acid sequences of (A and B) MBP-TAT-melusin (SEQ ID NOs: 7 and 8) and (C and D) MBP-melusin-TAT (SEQ ID NOs: 9 and 10). MBP amino acidic sequence is underlined, TAT sequence is in bold, melusin amino acidic sequence is double underlined, TEV protease cleavage site is indicated by a dotted line. (E and F) Schematic representation of the cloning strategy used to insert melusin, TAT and TEV coding sequences in pMAL vectors.
FIG. 1F-*nucleotides* 1076-1149 of SEQ ID NO:9 and amino acids 365-383 of SEQ ID NO:10.) (G) Coomassie stainings of total protein extracts from *E. coli* producing MBP-melusin-TAT (left) and MBP-TAT-melusin (right) fusion proteins; flow through after protein purification and elution fraction containing the purified proteins. (H) HPLC chromatogram of MBP-melusin-TAT eluted from a Resource Q ion exchange column (GE Helth-Care) with a gradient of 25 mM Tris-HCl pH7.5 to 25 mM Tris-FICl pH7.5 plus 1M NaCl. Protein elutes at 140 mM NaCl.
Figure 1H:
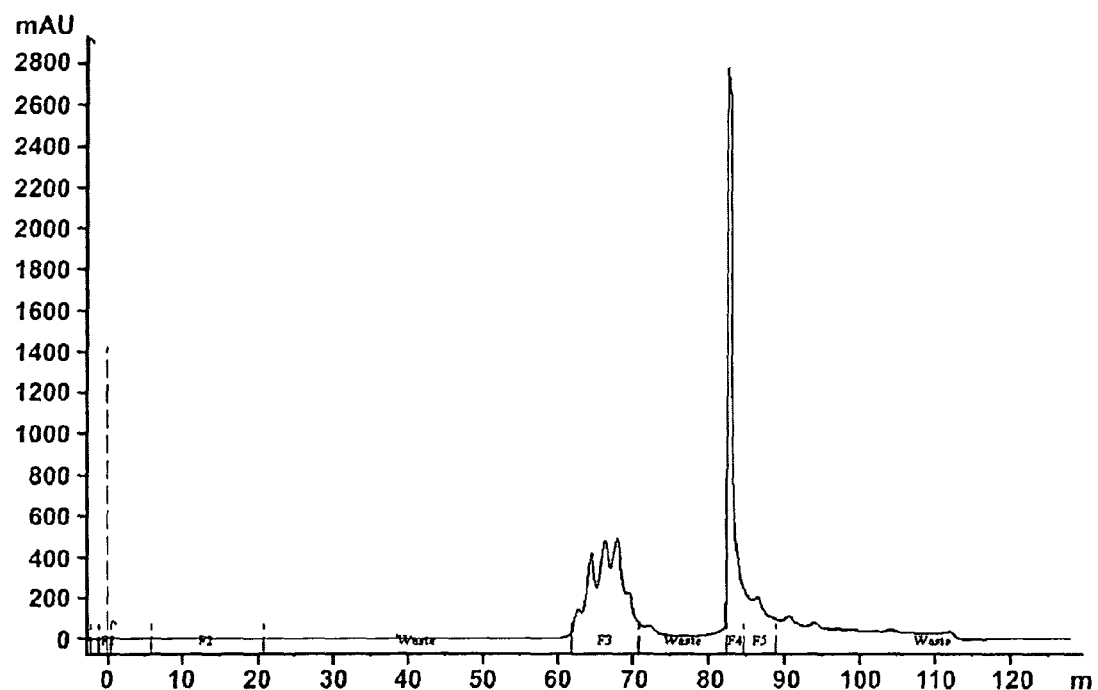

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment.

Furthermore, the particular features, structures, or characteristics may be combined in any suitable manner in one or more embodiments.

The headings provided herein are for convenience only and do not interpret the scope or meaning of the embodiments.

Recombinant proteins can be extremely useful biopharmaceutical products, but their production and subsequent purification often present a number of difficulties. In particular the solubility of the recombinant protein is very often a serious problem. The protein synthesized in large amount by bacteria or eukaryotic cells fall out of solution due to denaturation and incorrect folding leading to a biologically inactive product. When recombinant proteins are produced in soluble form a problem is represented by their stability in the cell and during the purification procedure. In fact, several recombinant proteins are highly instable and undergo various degree of degradation by proteolysis inside the cell or break down during the purification procedure due to trace contaminants. These are serious problems that need to be overcome Recombinant proteins to be utilized as pharmacological agent in vivo also have to be highly stable once injected in the leaving organism, where are easily catabolised and removed from circulation.

An additional problem is represented by proteins, such melusin, that need to penetrate inside the cells in order to exert their function. Cell penetration can be achieved by specific peptides that have membrane translocation capacity, however, the efficiency of these modification is strictly dependent on the folding of the protein and position of the peptide within the protein sequence.

The present invention overcome all of the above noted deficiencies in the art as it allows production of highly soluble protein, very stable both during purification and after in vivo administration. Moreover the protein efficiently penetrate into cells and it is endowed with potent in vivo activity on the heart both in basal and pathological conditions.

The present invention thus concerns a recombinant melusin fusion protein having an improved stability and an enhanced capability to reach intracellular compartments as compared to recombinant melusin in vivo, and further having heart hypertrophy inducement activity in vivo, wherein said protein comprises i) a human melusin protein having the amino acid sequence as defined in SEQ ID No.:1, or a homologue thereof having at least 60%, preferably at least 80%, more preferably at least 90% sequence identity to SEQ ID No.:1 and having the function of native melusin protein or a human melusin portion derived from SEQ ID No.:1 or homologue thereof having at least 60%, preferably at least 80%, more preferably at least 90% sequence identity of the melusin portion derived from SEQ ID No.:1 and having the function of native melusin protein and ii) a cell penetrating polypeptide.

In a particularly preferred embodiment the recombinant melusin fusion protein is represented by the nucleotide and amino acid sequences set forth in SEQ ID No.:9 (DNA construct) and 10, respectively.

The cell penetrating polypeptide may be selected among HIV-TAT polypeptide, disclosed i.a. in Vives et al., (1997), peptides from the homeodomain of antennapedia also known as penetrating or pAntp disclosed i.a. in Derossi et al., (1996); Derossi et al., (1994); and Brugidou et al., (1995); R7 peptide disclosed in Rothbard et al., (2000); KALA peptide disclosed in Wyman et al., (1997); buforin 2 disclosed in Takeshima at al., (2003)); MAP disclosed in Oehlke et al., (1998); trasportan disclosed in Pooga et al., (1998); trasportan 10 disclosed in Soomets at al., (2000); pVEC disclosed in Elmquist at al., (2001); MPG peptide disclosed in Morris et al., (1997). The corresponding sequences of the above referenced cell penetrating polypeptides are shown in FIG. 6 and set forth in SEQ ID No.:11 to 20.

The recombinant melusin fusion protein can, then, be conjugated to the N-terminus to a tag protein, which can be selected among maltose-binding protein (MBP), glutathione S-transferase (GST), hexa Histidine peptide (HIS), Flag epitope, Myc epitope, Ig domain, staphylococcal protein A, or any protein sequence suitable to facilitate expression and purification of the recombinant protein.

The recombinant melusin fusion protein described herein is suitable for parenteral administration to a subject in need thereof in an amount of 1 to 100 mg/day.

The recombinant melusin fusion protein can be advantageously used as a medicament for the treatment of heart pathologies, like for example heart failure, and cardiomyopathy caused by aortic stenosis, chronic arterial hypertension, valvular dysfunction, myocardial infarct, myocarditis or idiopathic cardiomyopathy.

Heart failure can originate from many cardiac insults, among which aortic stenosis, valve dysfunction, viral or autoimmune myocarditis, chronic hypertension, myocardial infarction and genetic mutations. All these insults generate work overload on the cardiac muscle that on the long term leads to negative remodelling characterized by thinning of the ventricle walls, dilation of the ventricular chamber and loss of contractile function, features that typically define the pathological status known as heart failure.

In view of the therapeutic effects exerted by the recombinant fusion protein melusin disclosed herein, and more specifically in counteracting a) thinning of the ventricle walls, b) dilation of the ventricular chamber and c) loss of contractile function i.e. heart hypertrophy inducement activity in vivo, the recombinant fusion protein melusin can be of therapeutic efficacy in heart failure generated by all the above listed aetiologies.

In the following the invention will be described in connection to some specific embodiments, and more preferably to a cell-penetrating, recombinant human melusin protein MBP-Melusin-TAT, without any limiting effect on the scope of the ensuing claims.

The present disclosure concerns generation and purification protocols for a cell-penetrating, recombinant human melusin protein, MBP-Melusin-TAT in prokaryotic cells. The protein consists of a tag component, namely maltose binding protein (MBP) allowing effective protein folding and convenient affinity purification, the melusin sequence and the cell transduction domain from TAT protein of the HIV virus, conferring the ability to the recombinant protein to enter the cells.

The purification protocol consists of two phases: an affinity chromatography step based on the affinity of MBP for amilose and an ion-exchange chromatography allowing further purification and elimination of the LPS component.

MBP-melusin-TAT after incubation with cells in culture clearly enter cells and localizes in the cytoplasm. The signal was much less intense for the MBP-TAT-melusin protein indicating that the recombinant protein with C-terminal TAT sequence was more efficient in entering cell membrane. At the same time MBP-melusin, lacking TAT, sequence was not detectable inside the cells demonstrating the efficacy of the transduction domain in delivering the recombinant protein inside the cell (FIG. 2A).

The proliferation curves of untreated cells does not change significantly from that of cells treated with MBP-melusin-TAT demonstrating that the recombinant MBP-melusin-TAT has no cytotoxic effect on cells (FIG. 2B).

The purified recombinant MBP-Melusin-TAT protein is endowed with the ability to enter the cell, thus providing an effective intracellular delivery of melusin.

Figure 3:
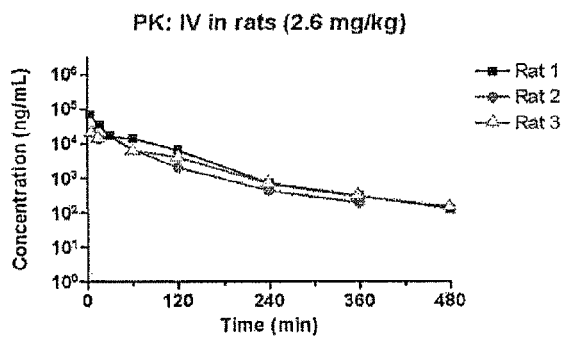
FIG. 3. Pharmacokinetics and biodistribution of recombinant MBP-melusin-TAT. Pharmacokinetic studies were performed both in rats (A) and mice (C) by intravenous and intraperitoneal administration of the protein respectively. Wistar rats were canulated in jugular vein and infused with 2.6 mg/Kg of purified MBP-Melusin-TAT. The concentration of MBP-Melusin-TAT protein in plasma was evaluated by both Elisa assay (A right panel) and Western Blotting (B). To evaluate the half-life of the protein after intra-peritoneum administration mice were injected with 5 mg/Kg of MBP-Melusin-TAT and the concentration of the protein in plasma was evaluated by Elisa (C). Recombinant MBP-Melusin-TAT protein has a 2 h half life both when administered intravenous or intraperitoneum (A and C). Moreover the protein is stable in circulation as detected by molecular weight analysis by western blotting of blood samples (B).
The biodistribution of the recombinant MBP-Melusin-TAT protein in mice was assessed after intraperitoneum injection with 5 mg/Kg every 4 hours for three times. Mice were sacrificed 4 hours after the last injection and perfused with PBS in the left ventricle to remove the protein still circulating in blood. Different organs were collected and protein extracts were analyzed by SDS-PACE and Western Blotting with melusin monoclonal antibodies specifically reacting with human recombinant melusin molecule (MAB-10333 Immunological Science www.immunologicalsciences.com). The protein present in each organ was quantified by determining the intensity of the bands (D). Western blot analysis of heart from mice injected under the same condition as above, with either MBP-Melusin-TAT (MMT) or with MBP-melusin lacking TAT (MM) as control (E). The recombinant protein containing TAT, but not the one lacking TAT, can be detected in heart 12 hours after injection consistently with the ability of the former one to enter cells in vivo. 24 hours after injection melusin level in the heart were still detectable (E lower panel) though at lower level compared to 12 hours. Vinculin antibodies were used as loading control.
Figure 3:
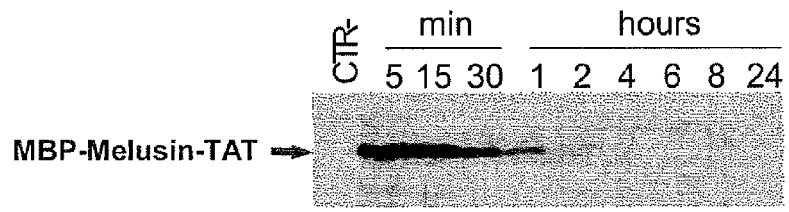
Figure 3:
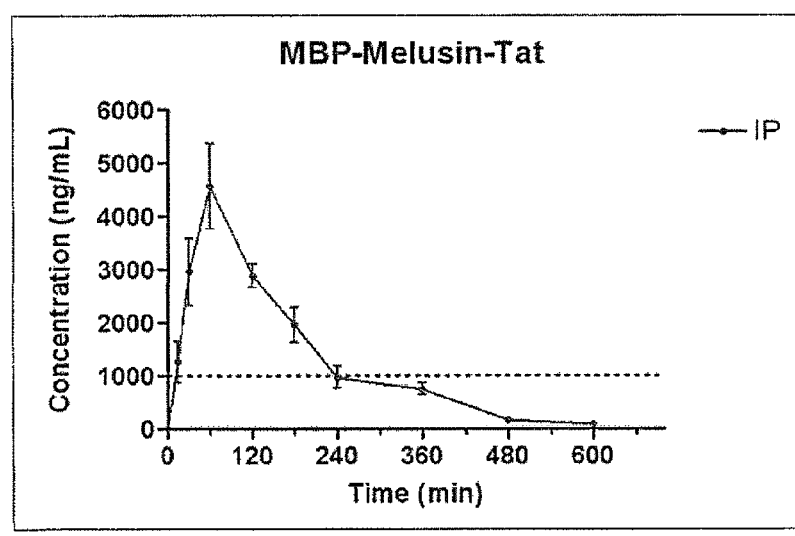

The purified recombinant MBP-Melusin-TAT protein has a 2 h half life when administered intravenous or intra-peritoneum in rats or mice (FIGS. 3A and 3C) and it is stable in circulation as detected by western blotting analysis of blood samples at 12 h after injection (FIG. 3B).

The distribution of the recombinant MBP-Melusin-TAT protein in vivo was assessed after intraperitoneum injection with 5 mg/Kg every 4 hours for three times. Mice were sacrificed 4 hours after the last injection and perfused with PBS in the left ventricle to remove the protein still circulating in blood. Different organs were collected and protein extracts were analyzed by SDS-PAGE and Western Blotting with melusin monoclonal antibodies specifically reacting with human recombinant melusin molecule (MAB-10333 Immunological Science www.immunologicalsciences.com) (FIG. 3D). The protein present in each organ was quantified by determining the intensity of the bands. Heart from mice injected with either MBP-Melusin-TAT (MMT) or with MBP-melusin lacking TAT (MM) under the same condition as above, were analyzed by SDS-PAGE and western blotting. The recombinant protein containing TAT, but not the one lacking TAT, can be detected in heart 12 hours after injection consistently with the ability of the former one to enter cells.

MBP-Melusin-TAT is devoid of toxic activity in mice treated for 15 day with a dose of 1 mg/day for a period of 15 days.

Figure 4:
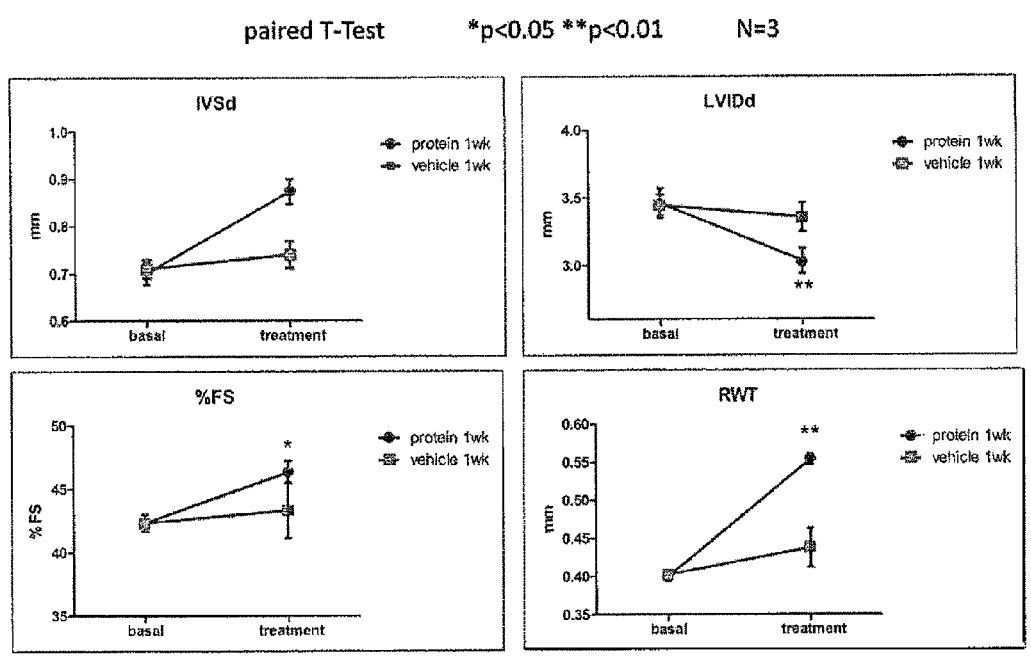
FIG. 4. Recombinant MBP-MELUSIN-TAT is pharmacologically active in mice and it induces compensatory concentric cardiac hypertrophy with increased contractility. Mice were injected intra-peritoneum for 7 days with a 1 mg/day/mouse of MBP-Melusin-TAT. Cardiac morphology and function was evaluated by echocardiography in each animal both before (basal) and after 7 days treatment (protein 1 wk). Mice treated with MBP-Melusin-TAT show increased septum thickness (IVSd), reduced diameter of the left ventricle chamber (LVIDd) accompanied by increased contractility as measured by fractional shortening (% FS). These features are typical of concentric remodelling defined by the relative wall thickness (RWT). No effect was observed in mice treated with vehicle alone (PBS).

Mice treated with a dose of 1 mg/day for a period of 7 days with MBP-Melusin-TAT develop a concentric remodelling of the left ventricle and increased contractility as detected by echocardiography analysis demonstrating the pharmacological activity of the recombinant protein in vivo (FIG. 4). More specifically, mice treated with MBP-Melusin-TAT show increased septum thickness (IVSd), reduced diameter of the left ventricle chamber (LVIDd) accompanied by increased contractility as measured by fractional shortening (% FS). These features are typical of concentric remodeling defined by the relative wall thickness (RWT). No effect was observed in mice treated with vehicle alone (PBS).

The therapeutical efficacy of MBP-Melusin-TAT (FIG. 5) was demonstrated in a pressure overload model of heart failure.

Figure 5:
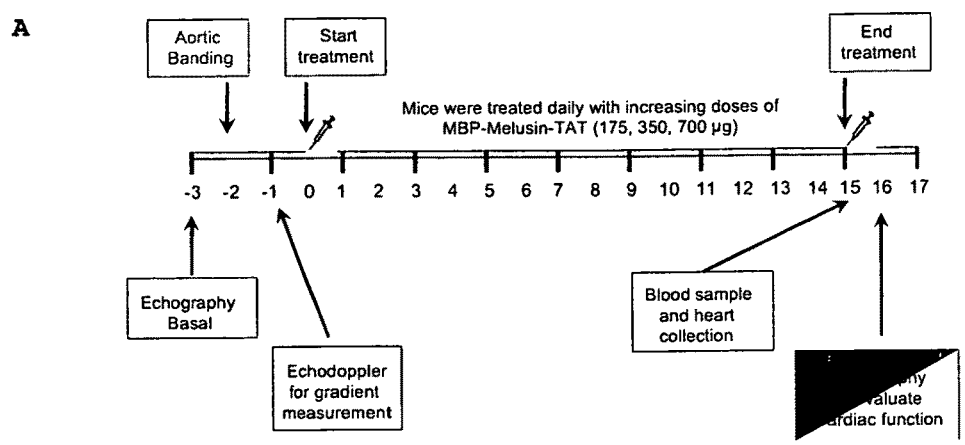
FIG. 5. Treatment with recombinant MBP-melusin-TAT results in improved left ventricular function in a model of pressure overload induced heart failure. The protocol illustrated in panel A was adopted to test efficacy of MBP-melusin-TAT in preventing heart failure. C57Black/N mice subjected to pressure overload by surgical banding of transverse aorta as previously described (Brancaccio et al., 2003). One day after aortic banding mice were treated by daily injections with increasing doses of MBP-melusin-TAT or PBS as vehicle control. Cardiac function and morphology were analyzed by echocardiography at day 1 after surgery and at the end of the treatment. Hearts were than explanted and examined at histological and biochemical level. 15 days after aortic banding mice treated with vehicle (PBS) develop left ventricle dilation (LVID) (panel B right columns PBS). However, treatment with recombinant MBP-melusin-TAT resulted in reduced left ventricle dilation (LVID) (panels B and C) and improved systolic function (C, right panel). The effect was directly proportional to the dose of MBP-melusin-TAT administered (B, C). Western blot analysis was performed to evaluate the concentration of MBP-melusin-TAT in the explanted heart. Interestingly, the amount of protein present in the heart 24 h after last treatment (panel D diamonds) was directly proportional to the contractile activity (panel D; EF % squares and FS % triangles).
Figure 5:
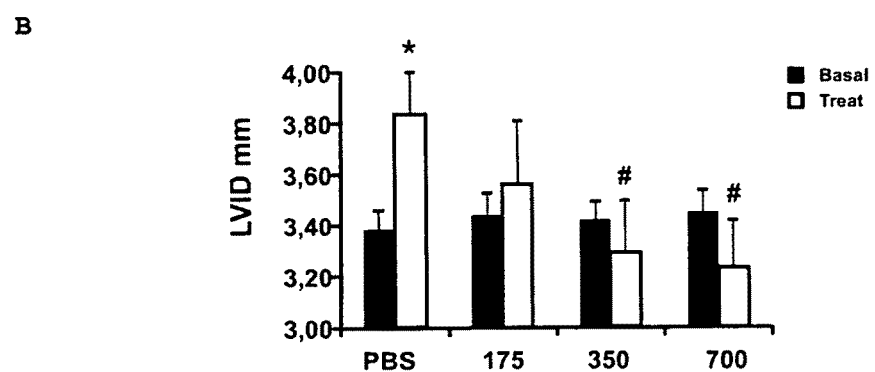
Figure 5:
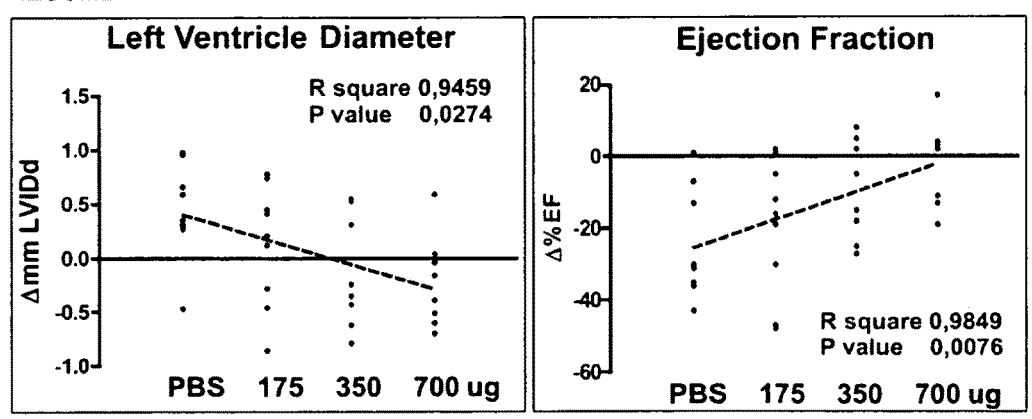

The protocol illustrated in panel A of FIG. 5 was adopted to test efficacy of MBP-melusin-TAT in preventing heart failure. C57Black/N mice were subjected to pressure overload by surgical banding of transverse aorta as previously described (Brancaccio et al., 2003). Only mice with a pressure gradient between 65-90 mm were selected for subsequent treatment (FIG. 5B). Four group of 9 mice each were treated respectively with 700 ug, 350 ug, 175 ug of MBP-melusin-TAT per day per mouse in 200 ul of PBS. A control group was treated with PBS alone. Treatment was prolonged for 15 days.

Cardiac function and morphology were analyzed by echocardiography at day 1 after surgery and at the end of the treatment. Hearts were than explanted and examined at histological and biochemical level. 15 days after aortic banding mice treated with vehicle (PBS) develop left ventricle dilation (LVID) (panel B right columns PBS of FIG. 5). However, treatment with recombinant MBP-melusin-TAT resulted in reduced left ventricle dilation (LVID) (panels B and C of FIG. 5) and improved systolic function (FIG. 5C). The effect was directly proportional to the dose of MBP-melusin-TAT administered (B, C). Western blot analysis was performed to evaluate the concentration of MBP-melusin-TAT in the explanted heart. Interestingly, the amount of protein present in the heart 24 h after last treatment (panel D diamonds) was directly proportional to the contractile activity (panel D; EF % squares and FS % triangles).

EXAMPLES

Example I

Preparation of pMAL Constructs and Production and Purification of Recombinant Proteins The entire human melusin cDNA (SEQ ID No.:1) was cloned in pMal-C2 plasmid (New England Biolabs) (FIG. 1a) in EcoRI and SalI restriction sites. A oligonucleotide (TACG-GCCGCAAGAAACGCCGCCAGCGCCGCCGC—SEQ ID No.:2) coding 11 amino acids (YGRKKRRQRRR—SEQ ID No.:3) from the HIV virus TAT protein was inserted either at the beginning of melusin amino acidic sequence or at the end of melusin amino acidic sequence (FIG. 1 A, B). A second double strand oligonucleotide (GAAAACCTGTACTTC-CAGGGG—SEQ ID No.:4) coding for the cleavage site (EN-LYFQG—SEQ ID No.:5) of the TEV protease, a highly site-specific protease from the Tobacco Etch Virus, was inserted between maltose binding protein (SEQ ID No.:6) and melusin coding (SEQ ID No.:1) sequences.

The constructs (the nucleotide and amino acid sequences of which are set forth in SEQ ID No.:7 to 10, and shown in FIGS. 1A and 1B) described above were transformed in BL21E. coli and protein synthesis was triggered by adding IPTG. In particular cells were plated onto LB plates containing ampicillin and incubated overnight at 37° C. Colonies were inoculated into LB-Amp culture and grown overnight at 37° C. Overnight cultures were diluted 1:100 with prewarmed LB-Amp media and grown at 37° C. to an OD600 of 0.5-0.6. Protein expression was induced with addition of 0.1 mM isopropylthiogalactoside (IPTG; Sigma, St. Louis, Mo.) for 4 hours. Cells were centrifuged and resuspended in column buffer (20 mM Tris-HCl pH 7.4, 0.2M NaCl, 1 µM $ZnCl_2$) plus cocktail of protease inhibitor (Complete—Roche), and then freezed at −80° C. Bacterial cells were thaw and sonicated for 6 times for 10 seconds on ice. Cell extract was clarified by centrifugation and the supernatant was transferred in a new tube.

Purification of MBP-fusion proteins was performed by affinity chromatography on amylose/agarose beads followed by maltose elution according to manufacturer's instructions (New England Biolabs). Protein content in the eluted fractions was determined with Bradford assay and the protein quality was assessed by SDS-PAGE followed by coomassie blue staining (FIG. 1D).

The fusion protein has a molecular weight of 75 kd and its identity was confirmed by western blotting with both melusin antibodies and maltose binding protein antibodies. The degree of purity at this stage was 90% as determined by coomassie blue staining followed by densitometry.

The chromatographic profile of the MBP-TAT-melusin protein (FIG. 1D right panel) was reproducibly more heterogeneous with a number of bands with molecular weight lower than that of the intact protein indicative of protein degradation and instability. On the other hand the fusion protein coding for the MBP-melusin-TAT generated a much more stable molecule with only a minor proportion of degradation products (FIG. 1D left panel).

Example II

Ion Exchange Protein Purification and LPS Removal

The protein was dialyzed against 25 mM Tris-HCl pH7.5 at 4° C. Over night and then loaded on a 6 ml Resource Q ion exchange (GE HelthCare) HPLC column sufficient for approx 30-40 mg of protein.

After washing with 25 mM Tris-HCl pH7.5, bound protein was eluted with a gradient of 25 mM Tris-HCl pH7.5 to 25 mM Tris-HCl pH7.5 plus 1M NaCl. Protein elutes at 140 mM NaCl (FIG. 1E). The protein is than dialyzed against sterile PBS and concentrated to 1 mg/ml or more by Centricon centrifugation for animal injection.

Example III

Test for Cell Penetration of Fusion Proteins

Figure 2:
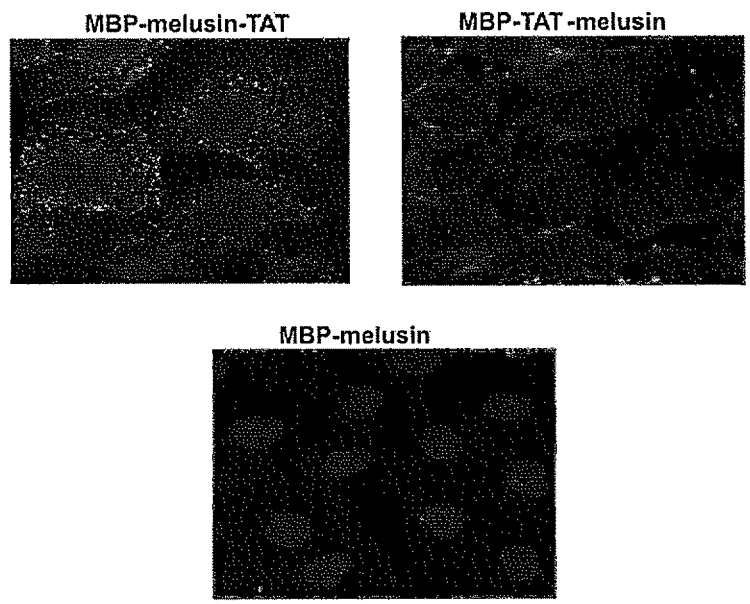
FIG. 2. (A) Ability of the recombinant MBP Melusin protein to enter in eukaryotic cells. COS cells grown in petri dishes were incubated with 50 μg/ml of recombinant MBP-melusin-TAT, MBP-TAT-melusin or MBP-melusin for 2 hours. After repeated washings with PBS, cells were fixed with detergent. Melusin was than visualized by immunofluorescence with confocal microscopy using 5E1 mouse monoclonal antibodies to human melusin (MAB-10333 Immunological Science www.immunologicalsciences.com) followed by RITC-labelled secondary anti mouse immunoglobulin. Pictures were taken with confocal microscope at fixed exposure time at focal planes inside the cytoplasm as can be visualized by the presence of nuclei stained with hoescht dye. MBP-melusin-TAT clearly localizes in the cytoplasm. The signal was much less intense for the MBP-TAT-melusin protein indicating that the recombinant protein with C-terminal TAT sequence was more efficient in entering cells. At the same time MBP-melusin, lacking TAT sequence was not detectable inside the cells demonstrating the efficacy of the transduction domain in delivering the recombinant protein inside the cell. (B) In vitro test of recombinant protein toxicity. COS cells were plated in 6 well dishes and incubated in plain culture medium (NT) or with 50 μg/ml of recombinant MBP-melusin-TAT or MBP-melusin for 0, 1, 2, 3, 4, 5 days and cell growth was determined by cell counting. The cell proliferation curves does not change significantly among different treatments demonstrating that the recombinant MBP-melusin-TAT has no cytotoxic effect on cells.
Figure 2:
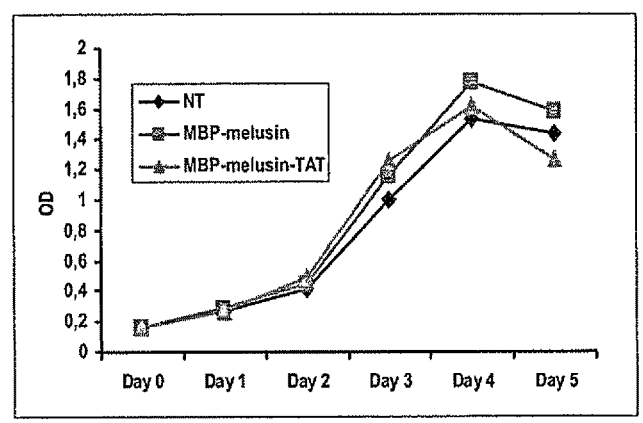

In order to investigate the ability of the recombinant MBP Melusin protein to enter in eukaryotic cells we treated COS cells with 50 µg/ml of recombinant MBP-melusin-TAT and another cell sample with MBP-melusin as control for 2 hours. Culture medium was removed and after repeated washings with PBS, cells were fixed with paraformaldheide and permeabilized with 0.1% Triton X100 in PBS. Cells were than incubated with 5E1 mouse monoclonal antibodies to human MELUSIN (MAB-10333, Immunological Science www.immunologicalsciences.com) (10 ug/ml for 1 h) followed by RITC-labelled secondary anti mouse immunoglobulin to assess the subcellular localization of the recombinant proteins. FIG. 2 shows COS cells treated for 2 hours with 50 µg/ml of recombinant MBP-melusin-TAT and analysed with confocal microscopy at focal planes inside the cytoplasm as can be visualized by the presence of nuclei stained with Hoechst dye. MBP-melusin-TAT is clearly in the cytoplasm mostly concentrated in dot like structures suggesting an endocytosis mediated uptake. On the contrary MBP-melusin lacking TAT sequence was not detectable inside the cells demonstrating the efficacy of the transduction domain in delivering the recombinant protein inside the cell. Interestingly the fusion protein containing the TAT sequence at melusin N-terminal (MBP-TAT-melusin) was significantly less efficient in entering, cell membranes (FIG. 2). For this reason we choose the MBP-melusin-TAT for the following experiments.

Example IV

Cell Toxicity Assay

To test the cytotoxicity of the treatment with the MBP-melusin-TAT we plated 50.000 COS cells/well in 6 well dishes. Cells were treated with 50 µg/ml of recombinant MBP-melusin-TAT for 0, 1, 2, 3, 4, 5 days and then analyzed for their proliferation ability and compared with untreated cells. Cells were fixed in 4% PFA, stained with crystal violet solution and the dye was recovered and subjected to spectrophotometric quantification. Our results demonstrated that the proliferation curves obtained for COS cells treated with MBP-melusin-TAT were not significantly different from that obtained for untreated cells (FIG. 2B). This experiment demonstrate that uptake from the culture medium of the MBP-melusin-TAT protein has not a cytotoxicity effect on cells in culture.

Example V

In Vivo Pharmacokinetic Studies

To establish the half-life of the protein in circulation in vivo pharmacokinetic studies were performed both in rats and mice by intravenous and intra-peritoneal administration of the protein. The following protocol was used for intravenous administration in rats:

Three Wistar rats were canulated in jugular vein and infused with 2.6 mg/Kg rat of purified MBP-Melusin-TAT. Blood was collected in EDTA as anti-coagulant at the following time points: 5-15-30 min; 1-2-4-6-8-24 hours after injection. The concentration of MBP-Melusin-TAT protein in plasma was evaluated by both Elisa assay and Western Blotting.

To evaluate the half life of the protein after intraperitoneum the following protocol was used: 5 mg/Kg of MBP-Melusin-TAT was injected in each mouse. Blood was in EDTA as anti-coagulant at the following time points: 0-0.25-0.5-1-2-4-6-8 hours. Four mice/each point were used Evaluation of MBP-Melusin-TAT protein concentration in plasma was obtained with Elisa assay Results indicated that the purified recombinant MBP-Melusin-TAT protein has a 2 h half life both when administered intravenous or intraperitoneum (FIGS. 3A and C). Moreover the protein is stable in circulation as detected by molecular weight analysis by western blotting of blood samples (FIG. 3B, western blot in heart).

Example VI

Biodistribution of MBP-Melusin-TAT

In order to assess the distribution of the recombinant MBP-Melusin-TAT protein in vivo, mice were injected IP with 5 mg/Kg every 4 hours for three times reaching a Plasmatic C max of 50 µg/ml and a C min of 10 µg/ml for a total time of exposition of 12 hours. MBP-melusin lacking TAT (MM) was used as control. Mice were than sacrificed and blood was collected in anticoagulant. After perfusion with PBS in the left ventricle to remove circulating blood different organs were collected and protein extracts were prepared with Triton x100 0.5% TBS buffer to quantify MBP-Melusin-TAT by Western Blot with melusin monoclonal antibody (www.immunologicalsciences.com MAB-10333). As shown in FIG. 3D E, MBP-Melusin-TAT (MMT), but not MBP-Melusin lacking TAT (MM), can be detected in heart and in other organs 12 hours after injection.

Example VII

Recombinant MBP-MELUSIN-TAT is Pharmacologically Active in Mice and it Induces Concentric Cardiac Remodelling with Increased Contractility To test the in vivo functional activity of recombinant melusin, mice were treated for 7 days with a 1 mg/day/mouse of MBP-Melusin-TAT administered by intra-peritoneal injection. To asses cardiac morphology and function mice were subjected to echocardiography with high resolution VEVO 770 apparatus equipped with the cardiac probe 707B. Each animal was examined both before and after treatment to directly compare the functional response. As shown in FIG. 4, mice treated with MBP-Melusin-TAT reduced diameter of the left ventricle chamber (LVIDd)) accompanied by increased contractility as measured both by fractional shortening (FS %). No effect was observed in mice injected with vehicle alone (PBS). These features, typical of concentric remodelling (RWT), demonstrate the pharmacological activity of the recombinant protein in vivo. (FIG. 4)

Example VIII

Treatment with Recombinant Melusin Results in Improved LV Function in a Model of Pressure Overload Induced Heart Failure The therapeutical efficacy of MBP-Melusin-TAT was demonstrated in a mouse model of pressure overload induced heart failure. C57Black/N mice were selected for these studies on the base of their high susceptibility to develop left ventricle dilation in response to pressure overload induced by surgical banding of transverse aorta. Upon a mean pressure gradient of 80 mm, these mice develop dilated cardiomyopathy within 15 days. This mouse strain represent, thus, a very good model for two main reasons: 1—the high susceptibility to dilated cardiomyopathy allows to test the efficacy of a therapeutic agent in very stringent conditions; 2—the rapid evolution toward heart failure allow to assess the efficacy of treatment in much short time compared to conventional mice strains which develop left ventricle dilation in 8-12 weeks (De Acetis et al., 2005). Mice were than subjected to surgical ligation of the transverse aorta and the degree of banding was monitored 24 h later by echo-Doppler analysis. Only mice with a pressure gradient between 65-90 mm were selected for treatment. Four group of 9 mice each were treated respectively with 700 ug, 350 ug, 175 ug of MBP-melusin-TAT per day per mouse in 200 ul of PBS. A control group was treated with PBS alone. Treatment was prolonged for 15 days, Cardiac function and morphology were analyzed at day 1 after surgery and at the end of the treatment. Hearts were than explanted and examined at histological and biochemical level. FIG. 5A illustrate the protocol used.

Treated mice showed clear improvement of systolic function as measured by ejection fraction as well as decreased level of left ventricle dilation (FIG. 5B, C). The effect was directly proportional to the dose of melusin administered. Western blot analysis was performed to evaluate the concentration of MBP-melusin-TAT in the explanted heart. As shown in FIG. 5D, the amount of protein present in the heart 24 h after last treatment varied slightly from mouse to mouse and was directly proportional to the contractile activity. All together these data demonstrate that recombinant melusin administered IP is therapeutically active in a mouse model of heart failure of pressure overload.

Naturally, while the principle of the invention remains the same, the details of construction and the embodiments may widely vary with respect to what has been described and illustrated purely by way of example, without departing from the scope of the present invention.

REFERENCES

Brancaccio, M., et al. (2003). Melusin, a muscle-specific integrin beta1-interacting protein, is required to prevent cardiac failure in response to chronic pressure overload. Nat Med 9, 68-75.

Brancaccio, M., et al. (1999). Melusin is a new muscle-specific interactor for beta(1) integrin cytoplasmic domain. J Biol Chem 274, 29282-29288.

Brugidou, J., et al. (1995). The retro-inverso form of a homeobox-derived short peptide is rapidly internalised by cultured neurones: a new basis for an efficient intracellular delivery system. Biochem Biophys Res Commun 214, 685-693.

De Acetis, M., et al. (2005). Cardiac overexpression of melusin protects from dilated cardiomyopathy due to long-standing pressure overload. Circ Res 96, 1087-1094.

Degols, G., et al. (1989). Antiviral activity and possible mechanisms of action of oligonucleotides-poly(L-lysine) conjugates targeted to vesicular stomatitis virus mRNA and genomic RNA. Nucleic Acids Res 17, 9341-9350.

Derossi, D., et al. (1996). Cell internalization of the third helix of the Antennapedia homeodomain is receptor-independent. J Biol Chem 271, 18188-18193.

Derossi, D., et al. (1994). The third helix of the Antennapedia homeodomain translocates through biological membranes. J Biol Chem 269, 10444-10450.

Elmquist, A., et al. (2001). VE-cadherin-derived cell-penetrating peptide, pVEC, with carrier functions. Exp Cell Res 269, 237-244.

Lemaitre, M., et al. (1987). Specific antiviral activity of a poly(L-lysine)-conjugated oligodeoxyribonucleotide sequence complementary to vesicular stomatitis virus N protein mRNA initiation site. Proc Natl Acad Sci USA 84, 648-652.

Leonetti, J. P., et al. (1988). Antiviral activity of conjugates between poly(L-lysine) and synthetic oligodeoxyribonucleotides. Gene 72, 323-332.

Morris, M. C., et al. (1997). A new peptide vector for efficient delivery of oligonucleotides into mammalian cells. Nucleic Acids Res 25, 2730-2736.

Oehlke, J., et al. (1998). Cellular uptake of an alpha-helical amphipathic model peptide with the potential to deliver polar compounds into the cell interior non-endocytically. Biochim Biophys Acta 1414, 127-139.

Pooga, M., et al. (1998). Cell penetration by transportan. FASEB J 12, 67-77.

Rothbard, J. B., et al. (2000). Conjugation of arginine oligomers to cyclosporin A facilitates topical delivery and inhibition of inflammation. Nat Med 6, 1253-1257.

Soomets, U., et al. (2000). Deletion analogues of transportan. Biochim Biophys Acta 1467, 165-176.

Takeshima, K., et al. (2003). Translocation of analogues of the antimicrobial peptides magainin and buforin across human cell membranes. J Biol Chem 278, 1310-1315.

Vives, E., et al. (1997). A truncated HIV-1 Tat protein basic domain rapidly translocates through the plasma membrane and accumulates in the cell nucleus. J Biol Chem 272, 16010-16017.

Wyman, T. B., et al. (1997). Design, synthesis, and characterization of a cationic peptide that binds to nucleic acids and permeabilizes bilayers. Biochemistry 36, 3008-3017.

The invention claimed is:

1. A recombinant melusin fusion protein having an improved stability and an improved capability to reach intracellular compartments as compared to recombinant melusin in vivo, wherein said recombinant melusin fusion protein comprises:
   i) a cell penetrating polypeptide, and
   ii) a human melusin protein comprising the amino acid sequence encoded by the nucleotide sequence as defined in SEQ ID No:1,
   wherein the cell penetrating polypeptide is an HIV-TAT polypeptide and the cell penetrating polypeptide is conjugated to the C-terminus of the human melusin protein and
   wherein the N-terminus of the human melusin protein is conjugated to a tag sequence and the tag sequence is a maltose-binding protein (MBP).

2. A DNA construct coding for the recombinant melusin fusion protein according to claim 1.

3. A method of treating heart failure, cardiomyopathy or cardiac failure comprising administering to a patient in need thereof the recombinant melusin fusion protein according to claim 1 in an amount to effect said treating.

4. The method according to claim 3, wherein said treating is achieved by inducement of heart hypertrophy.

5. The method according to claim 3, wherein the patient is suffering pressure overload.

6. The method according to claim 3, wherein said recombinant melusin fusion protein is suitable for parenteral administration.

* * * * *